(12) United States Patent
Wang et al.

(10) Patent No.: US 7,704,517 B2
(45) Date of Patent: Apr. 27, 2010

(54) TOPICAL COSMETIC COMPOSITION CONTAINING HYBRID SILICONE COMPOSITE POWDER

(75) Inventors: James J. Wang, Stony Brook, NY (US); Jin L. Hung, Brooklyn, NY (US); Thomas J. Hrubec, Paramus, NJ (US); David Granatell, Franklin Lakes, NJ (US)

(73) Assignee: Grant Industries, Inc., Elmwood Park, NJ (US)

( * ) Notice: Subject to any disclaimer, the term of this patent is extended or adjusted under 35 U.S.C. 154(b) by 1740 days.

(21) Appl. No.: 10/791,326

(22) Filed: Mar. 2, 2004

(65) Prior Publication Data
US 2005/0112072 A1 May 26, 2005

Related U.S. Application Data

(60) Provisional application No. 60/519,785, filed on Nov. 13, 2003.

(51) Int. Cl.
*A61K 8/02* (2006.01)
*A61K 8/58* (2006.01)
*C08G 77/12* (2006.01)
*A61Q 5/12* (2006.01)

(52) U.S. Cl. .................. 424/401; 424/70.1; 424/70.121; 528/31

(58) Field of Classification Search ........................ None
See application file for complete search history.

(56) References Cited

U.S. PATENT DOCUMENTS

| | | | | |
|---|---|---|---|---|
| 5,115,020 A | * | 5/1992 | Muramoto et al. ............. | 525/74 |
| 5,173,290 A | * | 12/1992 | Halloran et al. ........ | 424/70.121 |
| 5,803,887 A | * | 9/1998 | Fukunaga .................... | 492/59 |
| 5,837,793 A | * | 11/1998 | Harashima et al. ............ | 528/29 |
| 6,153,698 A | * | 11/2000 | Kanno et al. ................. | 525/125 |
| 6,726,997 B2 | * | 4/2004 | Tamori et al. ................ | 428/447 |
| 7,256,232 B2 | * | 8/2007 | Lamaze et al. .............. | 524/430 |
| 2003/0152785 A1 | * | 8/2003 | Sanders et al. .............. | 428/447 |

FOREIGN PATENT DOCUMENTS

EP 315836 A2 * 5/1989

OTHER PUBLICATIONS

Tuncel Colloid and Polymer Science 2000 278:1126-1138.*
DeGrazia et al. Journal of Applied Polymer Science 1995 55:793-805.*
KSP Series Product Brochure (2000).*
Zhu Macromolecules 1996 29:2813-2817.*
Blondeau et al. Reactive and Functional Polymers 1995 27:163-173.*

* cited by examiner

*Primary Examiner*—Robert A Wax
*Assistant Examiner*—Caralynne Helm
(74) *Attorney, Agent, or Firm*—Jonathan Myers; Andrew Wilford

(57) ABSTRACT

The present invention relates to a topical cosmetic composition that has improved non-oily feel comprising: (a) a hybrid silicone composite powder having a spherical shape with particle diameter ranging from 2 to 10 μm, of which each particle has a composite structures consisting of two interpenetrating polymer networks of polydimethylsiloxane (PMS) and polymethylsilsesquioxane (PMSQ). These two interpenetrating polymer networks are joined together by physical entanglements instead of chemical bonds; (b) a volatile cosmetic fluid; (c) a silicone fluid with viscosity ranging from 2 to 350 cSt; (d) an oil base consisting of an oil, wax, oil gelling agent or the mixture thereof; (e) a surface active agent; (f) a cosmetic pigment; and (g) an optional aqueous gel containing glycerin, glycols and an aqueous thickening agent. The cosmetic composition provides an improved skin sensory feel and a superior matte finish, and is useful for skin treatment, makeup and personal hygiene products.

15 Claims, 2 Drawing Sheets

PMS Network

TOPICAL COSMETIC COMPOSITION CONTAINING HYBRID SILICONE COMPOSITE POWDER

CROSS REFERENCE TO RELATED APPLICATION

This application is related to provisional application No. 60/519,785 filed 13 Nov. 2003.

FIELD OF THE INVENTION

The present invention relates to a topical cosmetic composition containing a hybrid silicone composite powder having a spherical shape with particle diameter ranging from 2 to 10 µm, of which each particle has a composite structure consisting of two interpenetrating polymer networks of polydimethylsiloxane (PMS) and polymethylsilsesquioxane (PMSQ). The interpenetrating polymer networks are joined together by physical entanglements instead of chemical bonds.

BACKGROUND OF THE INVENTION

Cosmetic and skin care formulations involve the use of oils from animals, natural plants and organic synthesis to build a carrier for active ingredients and to set up a barrier against environmental influences such as dirt, chemicals and microorganisms and against the loss of endogenous substances such as natural fats and water. The oils could often cause an unpleasant oily, greasy feel on the skin. Consequently, a skilled cosmetic formulator often chooses to add powders of, for example, nylon, polymethylmethacrylate, polyurethane, silica and polymethylsilsesquioxane into cosmetic formulations to reduce the undesirable skin feel. While these powders provide a reasonable skin sensory and oil control benefit, they suffer the disadvantage of high cost and low efficacy. Their sensory feel is not obvious when they are used in liquid formulations at a level of about 10% or lower. But if their concentration in the formula is too high these powders lead to an undesirable texture and appearance.

Recently, silicone elastomer powder has found increased use in cosmetic formulations because it imparts a very smooth feel and absorbs a large amount of oil at a relative low concentration, resulting in a matte appearance. The preparation and cosmetic applications of silicone elastomer have been disclosed in Japanese Pat. JP 1190757, issued to Toru et al.; U.S. Pat. No. 4,987,169, issued to Kuwata et al.; U.S. Pat. No. 5,266,321, issued to Shukuzaki et al.; U.S. Pat. No. 5,919, 468, issued to Bara; and U.S. Pat. No. 6,524,598, issued to Sunkel et al. While the silicone elastomer has advanced the approach to battle the oily, greasy feel, it still suffers from an unsatisfactory performance. A wet, draggy feel is often observed in the initial application to the skin when a high viscosity silicone fluid or a vegetable oil is used in formulations.

It remains desirable to further improve the sensory feel of the delivery system for cosmetic applications. It would be especially desirable to have new systems carrying modified silicone powder to provide an improved dry-smooth feel.

OBJECTS OF THE INVENTION

Accordingly, it is a first object of this invention to provide a hybrid silicone composite powder having a spherical shape with particle diameter ranging from 2 to 10 µm, of which each particle has a composite structure consisting of the interpenetrating polymer networks of PMS and PMSQ. The said hybrid silicone composite powder exhibits improved dry-smooth feel while remaining the same thickening efficiency in cosmetic oils as silicone elastomers.

It is a second object of this invention to provide a cosmetic composition and methods fulfilling the benefits resulting from the use of hybrid silicone composite powder. The cosmetic composition of the present invention comprises: (a) a hybrid silicone composite powder; (b) a volatile cosmetic fluid; (c) a silicone fluid with viscosity ranging from 2 to 350 cSt; (d) an oil base consisting of an oil, wax, oil gelling agent or the mixture thereof; (e) a surface active agent; (f) a cosmetic pigment; and (g) an optional aqueous gel containing glycerin, glycols and an aqueous thickening agent.

It is a third object of this invention to provide a stable skin treatment composition that provides an improved dry-smooth feel with matte appearance.

It is a fourth object of this invention to provide a stable make-up composition that provides a unique sponge touch and a smooth, powdery feel.

It is a fifth object of this invention to provide a personal hygiene composition that provides an improved fresh, smooth skin feel.

SUMMARY OF THE INVENTION

The cosmetic composition of this invention is characterized by the fact that it contains from 0.5 to 40% of the hybrid silicone composite powder, which is the (a) component of the present invention, having a spherical shape with a particle diameter ranging from 2 to 10 µm, of which each particle has a composite structure consisting of two interpenetrating polymer networks of PMS and PMSQ. The two interpenetrating polymer networks are joined together by physical entanglements instead of chemical bonds, and cannot be separated from each other unless each network is broken. By optimizing the weight ratio of two polymer networks in the composite structure, the individual polymer properties are changed, resulting in a new material with novel properties.

Unless otherwise indicated, all percentages and ratios are by weight. All weight percentages are calculated on the basis of the total weight of the composition.

The present inventors have surprisingly discovered that the hybrid silicone composite powder of the present invention has an improved dry-smooth feel similar to what PMSQ powder would provide while retaining the same or even better thickening efficiency to form a gel as the silicone elastomer. More surprisingly, the blend of PMSQ powder (Tospearl 145A, supplied by GE Silicones) and PMS powder (Gransil EP-LS, self-supplied) at the same weight ratio and concentration did not demonstrate a similar skin feel and failed to provide the expected viscosity as in the case of the hybrid silicone composite powder.

As is described above, the hybrid silicone composite powder has the most characteristic feature of the composite structure of two interpenetrating networks joined together by physical chain entanglements while it as a whole consists of dimethylsiloxane units and methylsilsesquioxane units expressed by the formulas of $(CH_3)_2SiO$ and $CH_3SiO_{1.5}$, respectively. The first network of PMS was prepared through the hydrosilylation reaction, which was well known in the art, between an organohydrogen polysiloxane and an alkenyl-functionalized organopolysiloxane in the presence of Karstedt's catalyst, which was disclosed in U.S. Pat. Nos. 3,715,334 and 3,419,593 incorporated herein by reference. The Karstedt's catalyst is a platinum divinyltetramethyldisiloxane complex, which is the reaction product of chloroplatinic acid and an organosilicon compound containing terminal aliphatic unsaturation. The level of the catalyst for effecting the hydrosilylation reaction is usually from 2 to 50 ppm relative to the total weight of the silicone reactants. The second network of PMSQ was prepared by hydrolization reaction of methylalkoxysilane with aqueous ammonia as the catalyst, followed by condensation at an elevated temperature. In order to obtain the composite structure of interpenetrating polymer networks, methylalkoxysilane had to be impregnated in the PMS network and subjected to hydrolysis-condensation reaction to form the second network within the first network. This impregnation was carried out by: (1) presenting methylalkoxysilane in the reaction mixture while PMS network was being formed; or (2) introducing methylalkoxysilane into the PMS network through a swelling process.

The method for producing the hybrid silicone composite powder is not particularly limited. In a preferred embodiment, it is produced by sequentially synthesizing PMS and PMSQ networks to obtain a pre-cured hybrid silicone composite particle emulsion, followed by spray drying the emulsion. While the PMS network can be made by using other reactions such as condensation reaction and free radical reaction, in a preferred embodiment the network is prepared by using a hydrosilylation reaction between an alkenyl organopolysiloxane and organohydrogen polysiloxane. In general, the alkenyl organopolysiloxane is an organopolysiloxane having two or more alkenyl groups per molecule on average and can be represented by the formula:

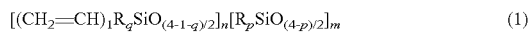  (1)

where q is a number ranging from 1 to 2; p is a number ranging from 1 to 3; n is a number equal to or greater than 2, preferably ranging from 2 to 10, more preferably ranging from 2 to 5, most preferably ranging from 2 to 3; m is a number greater than 0, preferably ranging from 5 to 350, more preferably ranging from 8 to 180, most preferably ranging from 80 to 120. R is an alkyl group selected from methyl, ethyl, propyl, phenyl or the like, preferably from methyl, ethyl and phenyl, more preferably from methyl and phenyl. The organohydrogen polysiloxane is an organopolysiloxane having two or more silicon-hydride groups, Si—H, per molecule on average and can be represented by the formula:

  (2)

where q is a number ranging from 1 to 2; p is a number ranging from 1 to 3; n is a number equal to or greater than 2, preferably ranging from 2 to 10, more preferably ranging from 2 to 5; ma is a number greater than 0, preferably ranging from 5 to 200, more preferably ranging from 8 to 100, most preferably ranging from 25 to 50. R is an alkyl group selected from methyl, ethyl, propyl, phenyl or the like, preferably from methyl, ethyl and phenyl, more preferably from methyl.

In a preferred embodiment, the hydrosilylation reaction (or referred to as curing reaction) is carried out with Karstedt's catalyst at a level from 2 to 50 ppm relative to the total weight of the silicone reactants at room temperature. The curing reaction usually completes within 24 hours depending on the molecular weight of each functional organopolysiloxane and the molar ratio of Si—H to CH$_2$=CH— groups. In general, the molar ratio of Si—H to CH$_2$=CH— groups can be ranged from 1:3 to 3:1. The higher the ratio, the faster the curing undergoes. Preferably, the ratio ranges from 1:1 to 3:1, more preferably from 2:1 to 3:1.

As is known in the art, methyltrialkoxysilane or their partially hydrolyzed condensates can be used to prepare PMSQ network in an aqueous solution of an alkaline earth hydroxide, an alkali carbonate, an aqueous solution of ammonia or an organic amine compound. A variety of methyltrialkoxysilanes such as methyltrimethoxysilane, methyltriethoxysilane, methyltripropoxysilane and methyltributoxysilane can be used as the starting material.

According to the present invention, the hybrid silicone composite powder was obtained by carrying out two sequential reactions. The first one was the hydrosilylation reaction of an emulsion of organohydrogen polysiloxane and vinyl-functional polydimethylsiloxane in the presence of the Karstedt's catalyst at room temperature for 24 hours. Methyltrimethoxysilane, which is the reactant for the second reaction, can be added in the emulsion before or after the hydrosilylation reaction. The hydrosilylation reaction takes place only between organohydrogen polysiloxane and vinyl-functional polydimethylsiloxane. The second reaction is the hydrolization-condensation reaction of methyltrimethoxysilane activated by the addition of aqueous ammonium solution at 15° C. for a period of 1 hour, followed by raising the temperature to 70° C. to promote condensation for 6 hours. The resulting reaction mixture was a hybrid silicone composite particle emulsion, which was diluted with water and spray-dried to a powder consisting of two interpenetrating polymer networks of PMS and PMSQ represented by formulae (3) and (4), respectively:

  (3)

  (4)

where pa is a number ranging from 1 to 2; $R^1$ is an ethyl, vinyl or hydrogen group; qa is a number ranging from 0 to 1; mb and na are numbers with a ratio of mb:na ranging from 1:10 to 10:1, preferably from 7:1 to 9:1, more preferably from 8:1 to 9:1. The numerical ranges for mb and na are chosen such that the hybrid silicone composite powder of the present invention will not be soluble in the solvents used.

Various volatile cosmetic fluids can be used without special limitation as the (b) component. It can be cyclomethicone fluid, 0.65 to 2.0 cSt dimethicone fluid, $C_8$ to $C_{12}$ hydrocarbon fluid, low molecular weight alkylmethicone fluid and the like. When swollen with volatile cosmetic fluids, the hybrid silicone composite powder provides a fresh feeling to the skin in addition to a superior dry-smooth sensory. The amount of the volatile fluid used varies in the range from 0.1 to 95% depending on the viscosity required for the composition.

Silicone fluids for the (c) component can be used either alone or in combination with the (b) component mentioned above. Without special restriction, silicone fluids can be selected from organopolysiloxane fluid with viscosity ranging from 2 to 350 cSt. Illustrative examples are the fluid of dimethicone, phenyltrimethicone, alkyldimethicone, silanol, amino-containing silicone, fluoroalkyl silicone, hydroxy-functional silicone, carboxyl-functional silicone, alkoxy-functional silicone, high molecular weight silicone gum solution, silicone resin solution, silicone-grafted polyacrylate solution and the like. The viscosity of the silicone fluid is a primary factor to determine the swelling ability. The higher the viscosity, the lower the swelling ability.

A variety of cosmetic oils, waxes and oil gelling agents from both natural and synthetic sources can be used for the (d) component without special limitation. Such oils, waxes and oil-gelling agents include plant oils, mineral oils, animal oils, fatty acids and their esters, fatty alcohols and the like. Illustrative examples of cosmetic oils may be liquid paraffin, petrolatum, squalane, jojoba oil, castor oil, cocoa butter, cottonseed oil, corn oil, almond oil, avocado oil, palm oil, sesame oil, soybean oil, kikui oil, lanolin oil, wheat germ oil, olive oil, isopropyl myristate, isostearyl palmitate, isononyl isononanoate, neopentyl glycol diheptanoate, $C_{12}$-$C_{15}$ alkyl benzoate and the like. Specific examples of cosmetic waxes are bees wax, microcrystalline wax, carnauba wax, candelilla wax, paraffin wax, serecin wax, hydrogenated castor oil, polyethylene wax, stearyl alcohol, cetyl alcohol, lauryl alcohol, myristic acid, stearic acid, ricinoleic acid, behenic acid and the like. Specific examples of oil-gelling agents are natural or synthetic montmorillonite minerals such as hectorite, bentonite and quaternized derivatives thereof which are obtained by reacting the minerals with a quaternary ammonium compound such as quaternized hectorite bentonites, for example, Quaternium-18 hectorite or the like. Also suitable as the non-wax gelling agents are polymeric materials, which generally contain a hydrophilic backbone and hydrophobic side groups. Examples include polyacrylates with $C_{12}$-$C_{18}$ alkyl side groups, cellulose ethers with $C_{12}$-$C_{18}$ alkyl groups, polyglyceryl fatty acid esters such as polyglyceryl-6 octastearate and glyceryl behenate/eicosadioate, starch-derived $C_{12+}$ fatty acid esters and hydrophobic sucrose fatty esters. Also suitable gelling agents are metallic soaps such as aluminum 12-hydroxystearate, calcium palmitate, calcium stearate and the like.

The surface active agent, which is the (e) component of the present invention, may be selected without special restriction from nonionic, anionic, cationic, amphoteric or oxyalkylene-modified organopolysiloxane. Illustrative examples of nonionic agents include alkylpolyglycosides such as cetearyl glucoside, myristyl glucoside and cocoyl glucoside fatty acid esters of sucrose such as sucrose tristearate, fatty acid esters of sorbitan such as sorbitan sesquioleate and sorbitan isostearate and alkoxylated fatty alcohols such as laureth-4, laureth-7, deceth-12 and steareth-10. Examples of anionic type surfactants are fatty acid soaps such as sodium lauryl sulfate, magnesium lauryl sulfate, ammonium lauryl sulfate, DEA-lauryl sulfate, sodium dodecylbenzenesulfonate, sodium $C_{14}$-$C_{16}$ olefin sulfonate and the like. Specific examples of cationic surfactants are cocotrimonium chloride, soytrimonium chloride, tallotrimonium chloride and cetrimonium chloride. Amphoteric surfactants are, for example, various types of betaines such as cocamidopropyl betaine, coco-betaine, cocamidopropyl hydroxysultaine and the like. The oxyalkylene-modified organopolysiloxanes can be, for example, polyether-modified silicones and alkyl-polyether-modified silicones.

Examples of the cosmetic pigment for the (f) component of the present invention are selected from, without special restriction, talc, kaolin, mica, magnesium carbonate, magnesium silicate, aluminum magnesium silicate, silica, calcium carbonate, zinc oxide, titanium dioxide, red iron oxide, yellow iron oxide, black iron oxide, ultramarine blue, polyethylene powder, polystyrene powder, silk powder, methacrylate powder, polytetrafluoroethylene powder, nylon powder, polyurethane powder, crystalline cellulose, starch, titanated mica, bismuth oxychloride, pearl, pearl mica, interference pigments and the like. The amount of the cosmetic pigment used for makeup compositions is usually from 0.05 to 40% depending on the intended purpose without restriction.

An aqueous gel containing glycerin, glycols and an aqueous thickening agent of the (g) component may be optionally included in the composition of the present invention to aid the cooling, moisturizing, viscosity adjusting and dissolution of active ingredients. Optionally, the (g) component further comprises a humectant selected from glycerin and polyhydric alcohols for moisturizing such as polyalkylene glycols and more preferably alkylene polyols and their derivatives. Specific examples are propylene glycol, dipropylene glycol, polypropylene glycol, polyethylene glycol, sorbitol, hydroxypropyl sorbitol, hexylene glycol, 1,3-butylene glycol, 1,2,6-hexanetriol, ethoxylated glycerin, propoxylated glycerin and mixtures thereof. The amount of humectant may range from 1 to 45%, preferably from 10 to 35%, most preferably from 20 to 30% by weight. The (g) component of present invention can further comprise a thickening agent selected, without special restriction, from water-soluble or water dispersible polymers that may be crosslinked. The hydrophilic polymers contain hydrophobic groups in such forms of sequences, graft or side group distributed randomly so that they allow considerable thickening of the medium even at a small concentration. The thickening is generated by the formation of aggregates between the hydrophobic groups of the polymer, which constitute physical cross-linking points between the macromolecular chains. Suitable examples are copolymers of acrylic acid and methacrylic acid such as polyacrylic acid, polymethacrylic acid, crosslinked copolymers of acrylic acid/$C_{10}$-$C_{30}$ alkyl acrylate, methacrylic acid/ethyl acrylate/alkyl acrylate copolymer, acrylic acid divinyl isodecanoate crosslinked copolymers, acrylic acid/vinylpyrrolidone lauryl methacrylate terpolymers, acrylic acid/lauryl (meth)acrylate copolymers and methacrylic acid/ethyl acrylate/polyoxyethylenated stearyl methacrylate terpolymers. These (meth) acrylic acid-based polymers form a gel in aqueous medium by neutralizing with an inorganic or organic base. Other suitable examples may be selected from natural materials, which may be modified, such as cellulose, starch, xanthan gum, agarose, hydroxyethylcellulose, carboxybutyl chitosan, carboxymethyl dextran, hydroxypropyl starch phosphate and the like. Depending on the type of polymers, the amount of thickening agents is usually in the range from 0.2 to 3.0%.

Mention may be made of any additive usually used in the field considered, such as fillers and/or pearlescent agents, antifoam agents, antioxidants, opacifiers, fragrances, preserving agents, cosmetic or pharmaceutical active agents, sunscreens, antiperspirant agents and self-tanning agents, each in an effective amount to accomplish its respective functions. A person skilled in the art may select these possible additional compounds in such an amount that the advantageous properties of the composition according to the present invention are not, or are substantially not, adversely affected by the addition envisaged. The compositions are not particularly restricted to any format: for example, gel, lotion, cream, foundation, loose powder, press powder, stick, soap and paste.

The invention is illustrated in the examples below, which are not intended to be restrictive. Examples 1 and 2 describe the preparation of the hybrid silicone composite powder used in the present invention. Examples 3 to 16 describe the topical cosmetic compositions. All parts and percentages referred to herein are by weight relative to the total weight of the composition and the viscosity referred to herein is at 25° C. unless otherwise indicated.

EXAMPLE 1

Preparation of Hybrid Silicone Composite Powder 980 parts of dimethylvinylsiloxy-terminal polydimethylsiloxane (vinyl group equivalent=6,000), 216 parts of polymethylhydrogensiloxane of 40 cP viscosity in which both the molecular chain ends were blocked with trimethylsiloxy groups, 17 parts of polyoxyethylene (9 mol) lauryl ether, 60 parts of methyltrimethoxysilane and 386 parts of ion-exchanged water were combined in a vessel and homogenized through a colloid mill until an emulsion was formed. The emulsion was transferred into a glass reaction flask equipped with a mechanic mixer. The hydrosilylation reaction between the vinyl-terminal polydimethylsiloxane and polymethylhydrogensiloxane was initiated by the addition of Karstedt's catalyst with mixing. The catalyst was 2% platinum divinylpolydimethylsiloxane complex, at an amount such that the platinum metal was 20 ppm with respect to the total weight of silicone reactants. After curing for 24 hours, the emulsion was converted into a viscous dispersion of silicone rubber particles consisting of PMS network and unreacted methyltrimethoxysilane. 220 parts of ion-exchanged water was added to the dispersion and further cooled down to 15° C. By adding 0.5 parts of 28% aqueous solution of ammonia to the dispersion, methyltrimethoxysilane impregnated in the silicone rubber particles was hydrolyzed for 1 hour at 15° C. The temperature was then raised to 70° C. for 6 hours to complete the condensation of methyltrimethoxysilane to form PMSQ network within the PMS network rubber particles. After diluting with 50 parts of water and homogenizing, the dispersion was dried with a spray dryer to yield the hybrid silicone composite powder having a spherical shape with particle diameter ranging from 2 to 10 µm as measured by scanning electronic microscope.

EXAMPLE 2

Figure 1:
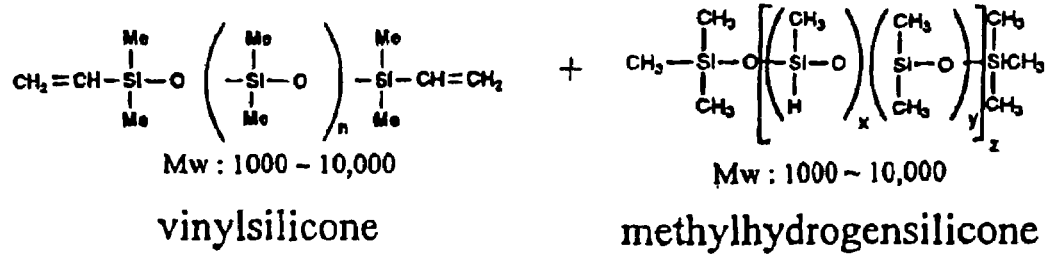
FIG. 1 shows the reaction scheme for preparing the polydimethylsiloxane (PMS) network by reacting a vinylsilicone having a molecular weight of 1000 to 10,000 with a methylhydiogensilicone having a molecular weight of 1000 to 10,000, in the presence of a platinum catalyst.
Figure 1:
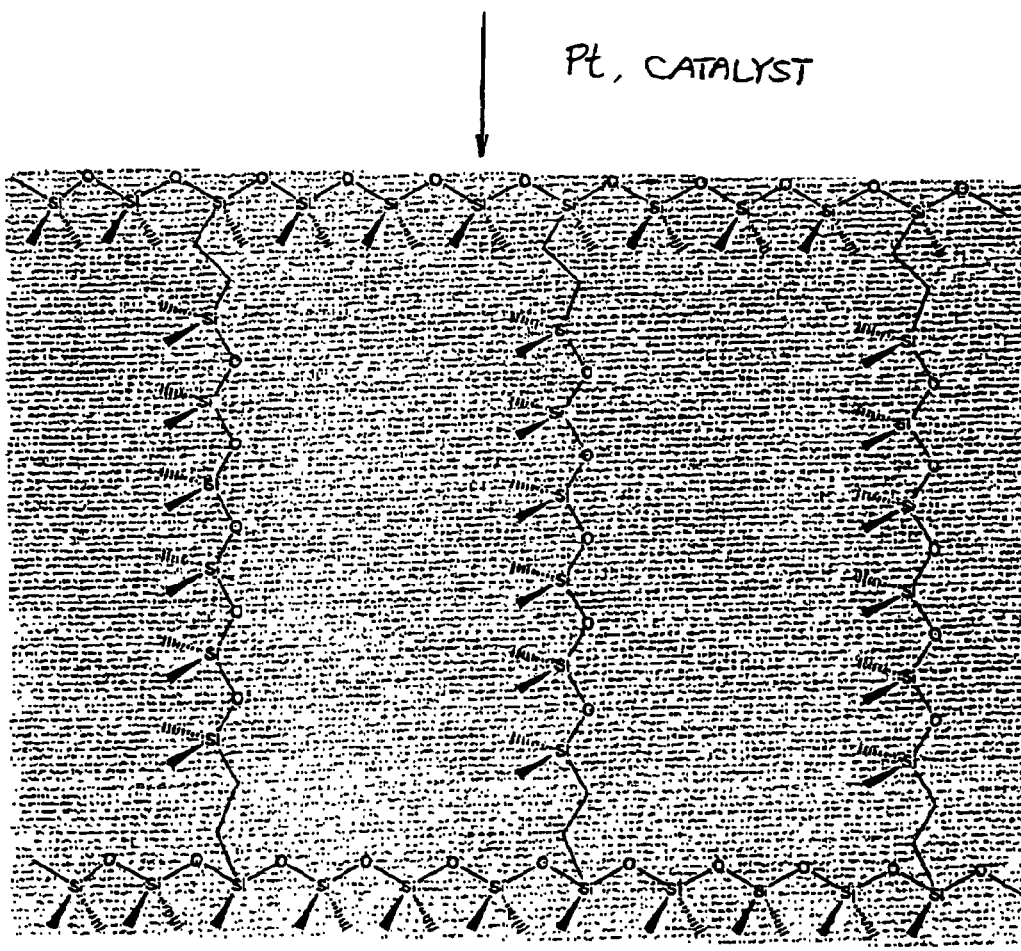
Figure 2:
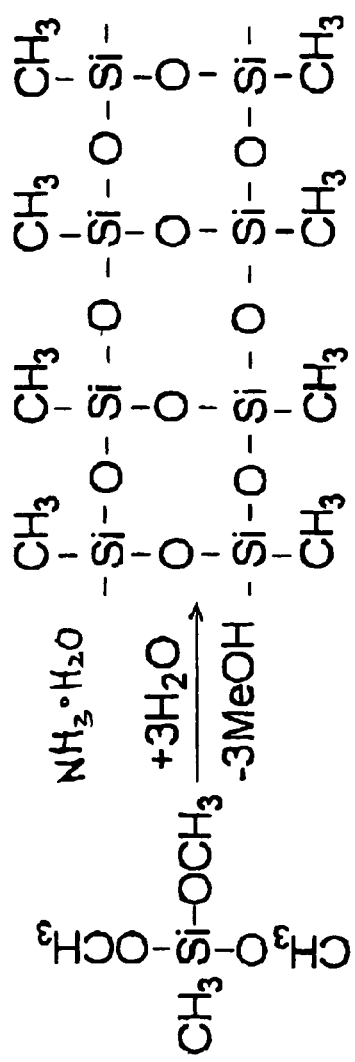
FIG. 2 shows the reaction scheme for preparing the polymethylsilsesquioxane (PMSQ) by reacting methyltrimethoxysilane with an aqueous solution of ammonia to undergo condensation reaction.

Preparation of Hybrid Silicone Composite Powder 300 parts of dimethylvinylsiloxy-terminal polydimethylsiloxane (vinyl group equivalent=4,000), 65 parts of polymethylhydrogensiloxane of 40 cP viscosity in which both the molecular chain ends were blocked with trimethylsiloxy groups, 4.6 parts of polyoxyethylene (9 mol) lauryl ether and 150 parts of ion-exchanged water were combined in a vessel and homogenized through a colloid mill until an emulsion was formed. The emulsion was transferred into a glass reaction flask equipped with a mechanic mixer. The hydrosilylation reaction between the vinyl-terminal polydimethylsiloxane and polymethylhydrogensiloxane was initiated by the addition of Karstedt's catalyst with mixing. The catalyst was 2% platinum divinylpolydimethylsiloxane complex, in an amount such that the platinum metal was 20 ppm with respect to the total weight of silicone reactants. After curing for 24 hours, the emulsion was converted into a viscous dispersion of silicone rubber particles consisting of PMS network and diluted with 100 parts of ion-exchanged water. 46 parts of methyltrimethoxysilane was introduced to the mixture and homogenized through a colloid mill until methyltrimethoxysilane was totally absorbed into the silicone rubber particles. At 15° C., 0.3 part of 28% aqueous solution of ammonia was added to the mixture to activate the hydrolization reaction of methyltrimethoxysilane for 1 hour. The temperature was raised to 70° C. for 6 hours to complete the condensation of methyltrimethoxysilane to form PMSQ network within the PMS network rubber particles. After being diluted with 70 parts of water and homogenized, the mixture was dried with a spray dryer to yield the hybrid silicone composite powder having a spherical shape with particle diameters ranging from 2 to 10 µm as measured by scanning electron microscope.

EXAMPLE 3

Preparation of Silicone Gel

A translucent silicone gel useful as a base or component for cosmetic topical applications was prepared by blending together the powder prepared in Example 1, dimethicone fluid, cyclomethicone fluid, water or a mixture thereof. The viscosity of the silicone gel is dependent on the concentration of the powder used and the penetration ability of the fluids used. Cyclomethicone and low viscosity dimethicone fluids (less than 5 cSt) have the most penetration ability to the powder prepared in Example 1 and yield a high viscosity gel. The silicone gel of the composition below demonstrated a very dry-smooth, non-oily, non-greasy feel and provided a unique matte appearance on skin, which was useful as a wrinkle line corrector and mattifier for face products.

| Ingredient | A | B | C | D |
| --- | --- | --- | --- | --- |
| Powder of Example 1 | 14.0 | 16.0 | 20.0 | 14.0 |
| Cyclopentasiloxane | 86.0 | 75.0 | — | — |
| Dimethicone, 1.5 cSt | — | — | — | 86.0 |
| Dimethicone, 5 cSt | — | — | 80.0 | — |
| D.I. Water | — | 9.0 | — | — |
| Viscosity* (cP) | 1,240,000 | 1,490,000 | 1,420,000 | 1,280,000 |

*Viscosity was measured on Brookfield DV-I+, Spindle TE, 0.3 rpm, and 1.0 minute.

EXAMPLE 4

Preparation of Glycerin Gel

This example demonstrates a glycerin gel composition typical of the present invention. All components were combined together and mixed until uniform.

| Ingredients | wt % |
| --- | --- |
| Powder of Example 2 | 23.00 |
| Glycerin | 76.30 |
| Fragrance | 0.50 |
| Preservative | 0.20 |
| | 100.00 |

EXAMPLE 5

Preparation of Body Lotion

This example demonstrates a body lotion composition for skin treatment typical of the present invention. Part (1) was combined in a vessel and subjected to homogenizing to form a smooth gel. Part (2) was combined in a separate vessel sequentially at 60° C. and homogenized until all the powders were dissolved. Part (3) was mixed in a separate vessel at 90° C. until all solids were melted and then cooled down to 40° C. Part (4) was added to part (1) and mixed until uniform. Parts (1) to (4) were combined and homogenized until uniform. Part (5) was added and homogenized until uniform at 40° C. This exemplified formula demonstrated a dry-smooth feel and non-oily, non-greasy appearance, and was useful for skin treatment products.

|   | Ingredients | wt % |
|---|---|---|
| Part 1 | Powder of Example 1 | 4.00 |
|   | Cyclopentasiloxane | 26.00 |
| Part 2 | D.I. Water | 45.60 |
|   | Na Hyaluronate, 1% | 10.00 |
|   | Ascorbyl Glucoside | 2.00 |
|   | N-Acetyl-D-Glucosamine | 0.05 |
|   | Dismodium EDTA | 0.10 |
|   | Sodium Hydroxide, 50% | 0.45 |
|   | Magnesium Ascorbyl Phosphate | 0.20 |
|   | Hydrolyzed Rice Extract | 0.25 |
| Part 3 | Granthix APP (30% Ammonium Polyacryloyldimethyltaurate in oils) | 3.00 |
| Part 4 | Polysorbate-40 | 2.50 |
|   | Glycyrrhetinic Acid | 0.20 |
|   | Cholesterol | 0.20 |
|   | Grape Seed Oil | 1.00 |
|   | Myristyl Alcohol | 1.25 |
| Part 5 | Green Tea Extract | 0.20 |
|   | Yeast Extract | 1.00 |
|   | Tocopheryl Acetate | 0.20 |
|   | Linoleic Acid | 0.10 |
|   | Pigment | 0.80 |
|   | Preservative | 0.70 |
|   | Fragrance | 0.20 |
|   |   | 100.00 |

EXAMPLE 6

Preparation of Face Cream

This example demonstrates a cream composition for skin treatment typical of the present invention. Part (1) was combined in a vessel and subjected to homogenizing to form a smooth gel. Part (2) was combined in a separate vessel sequentially at 60° C. and homogenized until all the powders were dissolved. Part (3) was mixed in a separate vessel at 90° C. until all solids were melted and then cooled down to 40° C. Part (3) was added to Part (1) and mixed until uniform. Part (2) was added and homogenized until uniform. Part (4) was added sequentially and homogenized at 40° C. until uniform. This exemplified formula demonstrated a dry-smooth feel and non-oily, non-greasy appearance, and was useful as a cream for skin treatment products.

|   | Ingredient | wt % |
|---|---|---|
| Part 1 | Powder of Example 2 | 3.00 |
|   | Cyclopentasiloxane | 27.00 |
| Part 2 | D.I. Water | 45.60 |
|   | N-Acetyl-D-Glucosamine | 0.05 |
|   | Disodium EDTA | 0.10 |
|   | Na Hyaluronate, 1% | 10.00 |
|   | Sodium Hydroxide, 50% | 0.45 |
|   | Ascorbyl Glucoside | 2.00 |
|   | Magnesium Ascorbyl Phosphate | 0.20 |
|   | Hydrolyzed Rice Extract | 0.25 |
| Part 3 | Cetearyl Glucoside | 5.00 |
|   | PEG-100 Stearate | 0.50 |
|   | Glycyrrhetinic Acid | 0.20 |
|   | Cholesterol | 0.20 |
|   | Grape Seed Oil | 1.00 |
|   | Myristyl Alcohol | 1.25 |
| Part 4 | Green Tea Extract | 0.20 |
|   | Yeast Extract | 1.00 |
|   | Tocopheryl Acetate | 0.20 |
|   | Linoleic Acid | 0.10 |
|   | Pigment | 0.80 |
|   | Preservative | 0.70 |
|   | Fragrance | 0.20 |
|   |   | 100.00 |

EXAMPLE 7

Preparation of Cream

This example illustrates a cream composition for skin treatment typical of the present invention. Part (1) was combined in a vessel and subjected to homogenizing to form a smooth gel. Part (2) was mixed in a separate vessel at 70° C. until all the powders were melted. Parts (1) and (2) were combined and mixed until uniform. With mixing, Part (3) was added and homogenized until uniform. This exemplified formula had a unique creamy, dry-smooth feel and non-oily, non-greasy appearance and was useful as a cream for skin treatment products.

|   | Ingredients | wt % |
|---|---|---|
| Part 1 | Powder of Example 2 | 3.00 |
|   | Cyclopentasiloxane | 17.00 |
| Part 2 | Phenyltrimethicone | 2.00 |
|   | Sorbitan Tristearate | 1.00 |
|   | Cetyl Dimethicone Copolyol | 1.00 |
|   | Shea Butter | 1.00 |
|   | Propylene Glycol Dioctanoate | 5.00 |
|   | Isododecane | 5.00 |
|   | Preservative | 1.00 |
| Part 3 | D.I. Water | 62.00 |
|   | Sodium Chloride | 2.00 |
|   |   | 100.00 |

EXAMPLE 8

Preparation of Foundation

This example demonstrates a foundation composition for makeup typical of the present invention. Part (1) was combined in a vessel and subjected to homogenizing until no lumps were observed. Part (2) was combined in a separate vessel and pulverized to uniformity. Parts (1) and (2) were combined and mixed until uniform. With mixing, Part (3) was slowly added. The mixture was homogenized until uniform. Part (4) was added and homogenized until uniform.

| | Ingredients | wt % |
|---|---|---|
| Part 1 | Powder of Example 2 | 5.00 |
| | Dimethicone, 5 cSt | 14.50 |
| | Phenyltrimethicone | 2.00 |
| | Cyclopentasiloxane | 10.00 |
| | PEG-10 Dimethicone | 3.50 |
| | Propylene Glycol Dicaprylate/dicaprate | 6.00 |
| | Sorbitan Sesquioleate | 0.10 |
| Part 2 | Yellow Iron Oxide | 1.00 |
| | Red Iron Oxide | 0.30 |
| | Black Iron Oxide | 0.10 |
| | $TiO_2$ | 5.00 |
| | Mica | 5.00 |
| | Talc | 10.00 |
| Part 3 | D.I. Water | 34.20 |
| | Sodium Chloride | 2.00 |
| Part 4 | Preservative | 1.00 |
| | Quaternium-18 Hectorite | 0.30 |
| | | 100.00 |

EXAMPLE 9

Preparation of Spongy Mousse Blush

This example demonstrates a blush composition typical of the present invention. All ingredients were combined in order in a vessel and mixed slowly to uniformity. This exemplified formula demonstrated a unique spongy feel on finger touch and could be easily applied on the face with a very smooth feel.

| Ingredient | wt % |
|---|---|
| Powder of Example 2 | 31.64 |
| Petrolatum | 25.29 |
| Octyldodecyl Neopentanoate | 33.00 |
| Gransil 530 (silicone blend) | 5.40 |
| Retinyl Palmitate | 0.20 |
| Tocopheryl Acetate | 0.20 |
| D&C Red 7 Ca Lake As | 0.17 |
| Pigments | 4.10 |
| | 100.00 |

EXAMPLE 10

Preparation of Spongy Mousse Foundation

This example demonstrates a foundation composition typical of the present invention. All ingredients were combined in order in a vessel and mixed slowly to uniformity. This exemplified formula demonstrated a unique spongy feel to the touch and could be easily applied on the face with a very smooth feel.

| Ingredient | wt % |
|---|---|
| Powder of Example 2 | 29.60 |
| Petrolatum | 23.50 |
| Octyldodecyl Neopentanoate | 31.52 |
| Gransil 530 (silicone blend) | 7.00 |
| Retinyl Palmitate | 0.20 |
| Tocopheryl Acetate | 0.20 |
| Yellow Iron Oxide | 0.70 |

| Ingredient | wt % |
|---|---|
| Red Iron Oxide | 0.21 |
| Black Iron Oxide | 0.07 |
| $TiO_2$ | 3.50 |
| Mica | 3.50 |
| | 100.00 |

EXAMPLE 11

Preparation of Lipstick

This example demonstrates a lipstick composition typical of the present invention. Part (1) was combined in a vessel and milled twice on a three-roll mill. Part (2) was combined in a separate vessel and mixed at 85° C. until all solids were melted. Parts (1) to (3) were mixed together at 85° C. and poured into components.

| | Ingredient | wt % |
|---|---|---|
| Part 1 | Powder of Example 2 | 2.00 |
| | Phenyltrimethicone | 18.00 |
| | Castor Oil | 15.00 |
| | $TiO_2$ | 7.00 |
| | Brown Iron Oxide | 0.30 |
| | D & C Red 21 | 0.10 |
| | D & C Red 7 | 0.60 |
| Part 2 | Candelilla Wax | 4.50 |
| | Synthetic Bees Wax | 16.00 |
| | Polyisobutene | 3.50 |
| | Polydecene | 8.20 |
| | Castor Oil | 5.00 |
| | Oleyl Alcohol | 5.00 |
| | Lanolin Oil | 4.50 |
| | Neopentyl Glycol Dicaprylate/dicaprate | 5.00 |
| | Propylparaben | 0.30 |
| Part 3 | Octyl Methoxycinnamate | 4.00 |
| | Tocopheryl Linoleate | 1.00 |
| | | 100.00 |

EXAMPLE 12

Preparation of Oil-Free Press Powder

This example demonstrates an oil-free press powder composition typical of the present invention. Part (1) was pulverized until the color was fully developed. Part (2) was added and mixed until thoroughly dispersed. The mixture was pre-pressed at 700 psi pressure and further pressed at 1000 psi pressure.

| | Ingredient | wt % |
|---|---|---|
| Part 1 | Powder of Example 2 | 10.00 |
| | Talc | 40.10 |
| | Magnesium Stearate | 1.00 |
| | Mica | 10.00 |
| | Bismuth Oxychloride | 20.00 |
| | Titanium Dioxide and Methicone | 10.40 |
| | Yellow Iron Oxide | 4.00 |
| | Red Iron Oxide | 0.90 |
| | Black Iron Oxide | 0.50 |

-continued

| | Ingredient | wt % |
|---|---|---|
| Part 2 | Octyl Palmitate | 2.80 |
| | Methylparaben | 0.20 |
| | Propylparaben | 0.20 |
| | | 100.00 |

EXAMPLE 13

Preparation of Mascara

This example demonstrates a mascara composition typical of present invention. Part (1) was homogenized until uniform. Parts (2) and (3) were separately mixed at 80° C. until all solids were melted. Parts (1) to (3) were combined and homogenized at 80° C. until uniform. The mixture was cooled with gentle mixing.

| | Ingredient | wt % |
|---|---|---|
| Part 1 | Cyclopentasiloxane | 27.00 |
| | Powder of Example 2 | 1.00 |
| Part 2 | Glyceryl Monostearate | 3.60 |
| | PEG-100 Stearate | 1.80 |
| | Bees Wax | 7.30 |
| | Carnauba Wax | 4.50 |
| | Granacrysil BAS (siliconeacrylate polymer) | 2.00 |
| Part 3 | D.I. Water | 40.60 |
| | 1,3-Butylene Glycol | 4.00 |
| | Hydroxyethylcellulose | 0.20 |
| | Pigment | 7.00 |
| | | 100.00 |

EXAMPLE 14

Preparation of Antiperspirant Stick

This example demonstrates an antiperspirant stick composition typical of the present invention. Part (1) was homogenized at room temperature in a vessel. Part (2) was mixed in a separate vessel at 90° C. until all solids were melted. Part (2) was added to Part (1) and mixed at 90° C. until uniform. The mixture was cooled to 60° C. and poured into components.

| | Ingredient | wt % |
|---|---|---|
| Part 1 | Cyclopentasiloxane | 45.00 |
| | Dimethicone, 5 cSt | 5.00 |
| | Powder of Example 2 | 1.00 |
| Part 2 | Aluminum Zirconium Tetrachlorohydrex/glycine | 21.00 |
| | Stearyl Alcohol | 19.00 |
| | Hydrogenated Castor Oil | 3.00 |
| | Talc | 4.00 |
| | Glyceryl Stearate/PEG-100 Stearate | 2.00 |
| | | 100.00 |

EXAMPLE 15

Preparation of Deodorant

This example demonstrates a deodorant composition typical of the present invention. Part (1) was homogenized at 70° C. until uniform. Part (2) was added and homogenized until uniform. The mixture was cooled to 60° C. and poured into components.

| | Ingredient | wt % |
|---|---|---|
| Part 1 | Propylene Glycol | 73.00 |
| | Sodium Stearate | 5.00 |
| | Sodium Laureth-13 Carboxylate | 6.00 |
| | PEG-90 Diisostearate | 2.00 |
| | Powder of Example 2 | 3.00 |
| Part 2 | D.I. Water | 9.45 |
| | Triclosan | 0.05 |
| | Fragrance | 1.50 |
| | | 100.00 |

EXAMPLE 16

Preparation of Soap

This example demonstrates a soap composition typical of the present invention. Part (1) was mixed at 70° C. until clear. Part (2) was added and homogenized until uniform. The mixture was poured into components.

| | Ingredient | wt % |
|---|---|---|
| Part 1 | Sodium Tallowate | 48.00 |
| | Sodium Cocoate | 12.00 |
| | D.I. Water | 9.80 |
| | Glycerin | 1.20 |
| Part 2 | Glycerin | 20.00 |
| | Fumed Silica | 8.00 |
| | Powder of Example 2 | 1.00 |
| | | 100.00 |

References Cited

| | | |
|---|---|---|
| JP 1190757 Japanese Patent Publication 2-22767 | Toru et al. | July 1989 |
| 4,987,169 | Kuwata et al. | January 1991 |
| 5,266,321 | Shukuzaki et al. | November 1993 |
| 6,524,598 | Sunkel et al. | February 2002 |
| 5,919,468 | Bara | June 1999 |
| 3,715,334 | Karstedt | February 1973 |
| 3,419,593 | Willing et al. | December 1968 |

What is claimed is:

1. A hybrid silicone composite powder having a spherical shape with a particle diameter ranging from 2 to 10 microns, as an ingredient for a cosmetic applied to skin, to impart a smooth feeling when the cosmetic is applied to the skin, comprising polydimethylsiloxane (PMS) and polymethylsilsesquioxane (PMSQ) networks, wherein the PMS and PMSQ networks form a composite structure of two interpenetrating polymer networks in which the PMS and PMSQ networks are held together by physical entanglements on a molecular scale without chemical bonding between them.

2. The hybrid silicone composite powder defined in claim 1, wherein the PMS and the PMSQ networks have a weight ratio of PMS:PMSQ ranging from 1:1 to 50:1.

3. The hybrid silicone composite powder defined in claim 1 wherein the PMS network is the reaction product of an alkenyl silicone and a hydrogen silicone and the PMSQ network is a polymer of a methyltrialkoxysilane.

4. The hybrid silicone composite powder defined in claim 3 wherein the alkenyl silicone is an organopolysiloxane having two or more alkenyl groups per molecule, the hydrogen silicone is an organohydrogen polysiloxane having two or more Si-H groups per molecule, and the methyltrialkoxysilane is methyltrimethoxysilane or methyltriethoxysilane.

5. A method for preparing a hybrid silicone composite powder having a spherical shape with a particle diameter ranging from 2 to 10 microns, as an ingredient for a cosmetic applied to skin, to impart a smooth feeling when the cosmetic is applied to the skin, comprising polydimethylsiloxane (PMS) and polymethylsilsesquioxane (PMSQ) networks, wherein the PMS and PMSQ networks form a composite structure of two interpenetrating polymer networks, in which the PMS and PMSQ networks are held together by physical entanglements on a molecular scale without chemical bonding between them, which comprises the steps of:
  (a) preparing a PMS network by forming a liquid rubber emulsion comprising an alkenyl silicone and a hydrogen silicone and curing the liquid rubber emulsion by hydrosilylating the alkenyl silicone with the hydrogen silicone in the presence of Karstedt's catalyst at a level of 2 to 50 ppm relative to the total weight of the alkenyl silicone and the hydrogen silicone at room temperature;
  (b) adding a methyltrialkoxy silane to the hydrosilylation reaction in step (a) before or after completion of the hydrosilylation in the presence of an aqueous ammonia solution at 15° C.;
  (c) following step (b) raising the temperature to about 70° C. to promote hydrolyzation-condensation of the methyltrialkoxy silane thereby forming a PMSQ network resulting in a hybrid silicone composite emulsion containing PMS and PMSQ networks; and
  (d) diluting the hybrid silicone composite emulsion with water and spray-drying the two polymer networks of PMS and PMSQ to form a hybrid silicone composite powder of PMS and PMSQ.

6. The method for preparing a hybrid silicone composite powder defined in claim 5 wherein according to step (a) the liquid rubber emulsion is an o/w emulsion.

7. The method for preparing a hybrid silicone composite powder defined in claim 5 wherein according to step (a) the alkenyl silicone contained in the liquid rubber emulsion used to prepare the PMS network is an organopolysiloxane having two or more alkenyl groups per molecule.

8. The method for preparing a hybrid silicone composite powder defined in claim 5 wherein according to step (a) the hydrogen silicone contained in the liquid rubber emulsion used to prepare the PMS network is an organohydrogen polysiloxane having two or more Si—H groups per molecule.

9. The method for preparing a hybrid silicone composite powder defined in claim 5 wherein according to step (b) the methyltrialkoxysilane is selected from the group consisting of methyltrimethoxysilane and methyltriethoxysilane.

10. The method for preparing a hybrid silicone composite powder defined in claim 5 wherein according to step (c) the PMSQ network is synthesized through hydrolyzing and condensing the methyltrialkoxysilane impregnated in the PMS network with an aqueous solution of ammonia or an amine as the catalyst.

11. A silicone gel useful as a base for a topical cosmetic composition, which comprises a blend of:
  (a) a hybrid silicone composite powder having a spherical shape with a particle diameter ranging from 2 to 10 microns, as an ingredient for a cosmetic applied to skin, to impart a smooth feeling when the cosmetic is applied to the skin, comprising polydimethylsiloxane (PMS) and polymethylsilsesquioxane (PMSQ) networks, wherein the PMS and PMSQ networks form a composite structure of two interpenetrating polymer networks, in which the PMS and PMSQ networks are held together by physical entanglements on a molecular scale without chemical bonding between them; and
  (b) a volatile cosmetic fluid.

12. The silicone gel useful as a base for a topical cosmetic composition defined in claim 11 wherein the volatile cosmetic fluid is selected from the group consisting of cyclomethicone fluid, dimethicone fluid, a $C_8$ to $C_{12}$ hydrocarbon fluid, an alkylmethicone fluid, and an organopolysiloxane with a viscosity ranging from 2 to 350 Cst.

13. A glycerine gel useful as a base for a topical cosmetic composition, which comprises a blend of:
  (a) a hybrid silicone composite powder having a spherical shape with a particle diameter ranging from 2 to 10 microns, as an ingredient for a cosmetic applied to skin, to impart a smooth feeling when the cosmetic is applied to the skin, comprising polydimethylsiloxane (PMS) and polymethylsilsesquioxane (PMSQ) networks, wherein the PMS and PMSQ networks form a composite structure of two interpenetrating polymer networks, in which the PMS and PMSQ networks are held together by physical entanglements on a molecular scale without chemical bonding between them; and
  (b) glycerine.

14. A topical cosmetic composition, which comprises:
  (a) an amount of the silicone gel defined in claim 11 effective to impart a smooth feeling of the cosmetic to the skin; and
  (b) at least one cosmetically effective ingredient for treating the skin.

15. A topical cosmetic composition, which comprises:
  (a) an amount of the glycerine gel defined in claim 13 effective to impart a smooth feeling of the cosmetic to the skin; and
  (b) at least one cosmetically effective ingredient for treating the skin.

* * * * *